United States Patent
Horvath et al.

(10) Patent No.: US 7,189,260 B2
(45) Date of Patent: Mar. 13, 2007

(54) VENTRICULAR ASSIST SYSTEM SECONDARY IMPELLER

(76) Inventors: David Horvath, 19770 Seminole Rd., Euclid, OH (US) 44117; Leonard A. R. Golding, 16650 Auburn Rd., Auburn Township, OH (US) 44026; William A. Smith, 5480 Lansbury La., Lyndhurst, OH (US) 44124

( * ) Notice: Subject to any disclaimer, the term of this patent is extended or adjusted under 35 U.S.C. 154(b) by 580 days.

(21) Appl. No.: 10/333,760

(22) PCT Filed: Mar. 19, 2001

(86) PCT No.: PCT/US01/40329

§ 371 (c)(1),
(2), (4) Date: Jul. 28, 2003

(87) PCT Pub. No.: WO01/72351

PCT Pub. Date: Oct. 4, 2001

(65) Prior Publication Data
US 2004/0047753 A1    Mar. 11, 2004

(51) Int. Cl.
*A61M 1/10* (2006.01)
(52) U.S. Cl. ............ 623/3.13; 600/16; 604/8; 623/3.1
(58) Field of Classification Search ............ 623/3.1, 623/3.13, 3.24; 604/8; 600/16
See application file for complete search history.

(56) References Cited
U.S. PATENT DOCUMENTS
5,405,251 A    4/1995  Sipin 5,947,703 A    9/1999  Nojiri et al.

FOREIGN PATENT DOCUMENTS

| DE | 196 26 244 A1 | 2/1998 |
| WO | WO 94/09274 | 4/1994 |
| WO | WO 99/15212 | 4/1999 |

OTHER PUBLICATIONS

S. Nakamura, W. Ding, W. A. Smith, and Leonard A. R. Golding, Blood Flow Analysis for the Secondary Impeller of an IVAS Heart Pump, (5 pgs.) Cleveland, Ohio, 1997.

Stanley B. Malanoski, Helen Belawski, David Horvath, William A. Smith and Leonard R. Golding, Stable Blood Lubricated Hydrodynamic Journal Bearing with Magnetic Loading, Cleveland, Ohio, (4 pgs.) 1998.

*Primary Examiner*—Robert Pezzuto
*Assistant Examiner*—Yun Haeng Lee
(74) *Attorney, Agent, or Firm*—Amster, Rothstein & Ebenstein LLP

(57) ABSTRACT

In a centrifugal flow blood pump, usable in left ventricular assist applications, blood is pumped from an inlet (16) to an outlet (22) by a primary impeller (18). A portion of the blood that enters the pump follows a secondary channel (24) where a secondary impeller (70) routes the blood to lubricate a bearing between an impeller assembly (14) and a post formed by a component of the pump housing. The unique shape of the secondary impeller (70) prevents blood stagnation and provides for a well-washed fluid bearing.

16 Claims, 5 Drawing Sheets

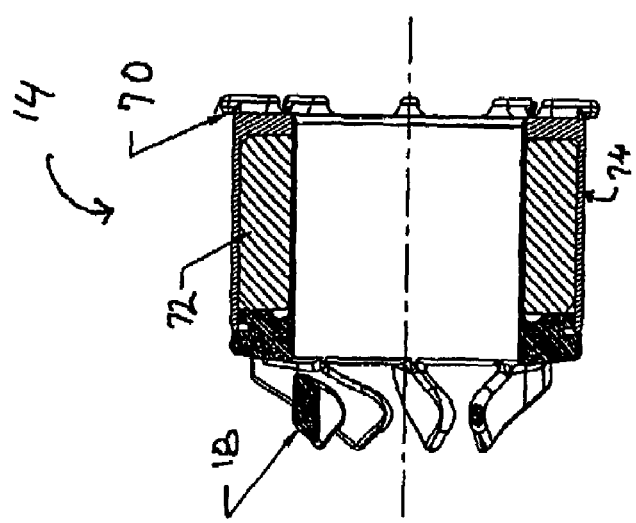
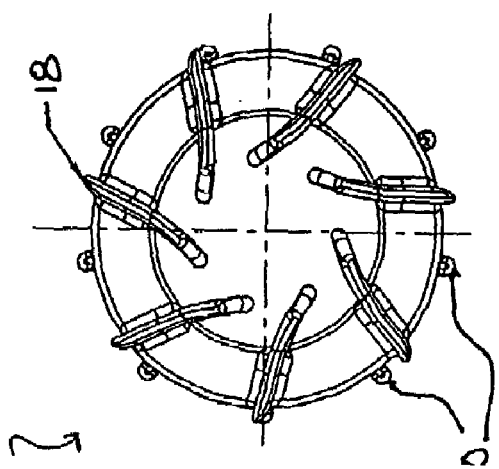
FIGURE 4B
FIGURE 4A

VENTRICULAR ASSIST SYSTEM SECONDARY IMPELLER

FEDERAL RESEARCH STATEMENT

The U.S. Government may have certain rights in this invention pursuant to contract number N01-HV-58159 awarded by the U.S. National Heart, Lung and Blood Institute of the National Institutes of Health.

BACKGROUND OF THE INVENTION

The present invention relates to the medical arts. It finds particular application in cardiac assist technologies using rotodynamic blood pumps, also known as left ventricular assist devices (LVAD) in assisting patients with failing hearts and will be described with particular reference thereto. It is to be appreciated that the present invention is also applicable to other types of pumps, and is not limited to the aforementioned application.

Rotodynamic pumps (axial flow, mixed flow, and centrifugal) have prospective applications in cardiac assist technologies. A typical cardiac assist system includes the blood pump itself, electric motor (usually a brushless DC motor integrated into the pump), drive electronics, microprocessor control unit, and an energy source, such as rechargeable batteries. These pumps can be used in fully implantable systems for chronic cardiac support where the whole system is located inside the body and there are no drive lines penetrating the skin. For more temporary support, the pump is located inside the body but some system components, including drive electronics and energy source, may be placed outside the patient body.

The inverted, shaftless, brushless motor design is utilized because it has a significant advantage over typical motor/drive shaft configurations. There are no openings in the housing that would allow blood into the motor, and the housing precludes air or other fluid from entering the bloodstream. A primary drive impeller of the pump encloses a drive magnet and is driven by a stator and coil assembly disposed radially inward from the motor rotor, i.e., an inverted motor. In order to avoid friction and subsequent heat buildup, the blood of the patient is used as a fluid bearing between the impeller and the stator.

A potential problem with this system is that the blood can become heated and/or stagnant, and partially solidify by forming a thrombus or heat coagulation of blood proteins on the stator housing surface or on the secondary impeller of the motor rotor in the inverted fluid film bearing assembly. Such a situation is undesirable and potentially life-threatening to the patient who is dependant on the proper function of such a device. Accordingly a need exists for a well-washed or continuous flow of blood that serves as the bearing between the rotor and stator components.

The present invention provides a new and improved method and apparatus that avoids thrombus and/or coagulated protein formation/deposition and overcomes the above referenced problems and others.

SUMMARY OF THE INVENTION

In accordance with one aspect of the present invention, a cardiac assist device is provided. A drive stator is received within a housing along with an impeller assembly. The impeller assembly includes primary and secondary impellers, and a drive rotor. The primary impeller provides a motive force which transports blood from an inlet port to an outlet port. The secondary impeller cycles blood to lubricate and cool a bearing between the impeller assembly and the stator housing.

In accordance with a more limited aspect of the present invention, the secondary impeller comprises radial vanes that exhibit symmetry relative to radii extending from a center of the impeller assembly.

In accordance with another aspect of the present invention, a left ventricular assist device is provided. A brushless DC motor and an impeller assembly are contained within a volute housing assembly. The impeller assembly comprises a primary impeller, an annular magnet drive rotor, and a secondary impeller. The secondary impeller comprises a plurality of radial vanes that are smooth and rounded, with an axial height at an outer radius greater than an axial height at an inner radius.

One advantage of the present invention is a blood pump with a single moving part with no seal between the motor and blood compartments.

Another advantage resides in avoiding problems associated with drive shaft interfaces.

Another advantage is the creation of blood flow and wash patterns that avoid the formation of blood element depositions.

Still further benefits and advantages of the present invention will become apparent to those skilled in the art upon a reading and understanding of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIG. 4A is an elevational view of an impeller assembly, particularly illustrating the primary impeller, in accordance with the present invention;

FIG. 4B is a cross-sectional view of the impeller assembly taken generally along the lines 4B—4B of FIG. 4A;

DETAILED DESCRIPTION OF THE PREFERRED EMBODIMENT

Figure 1:
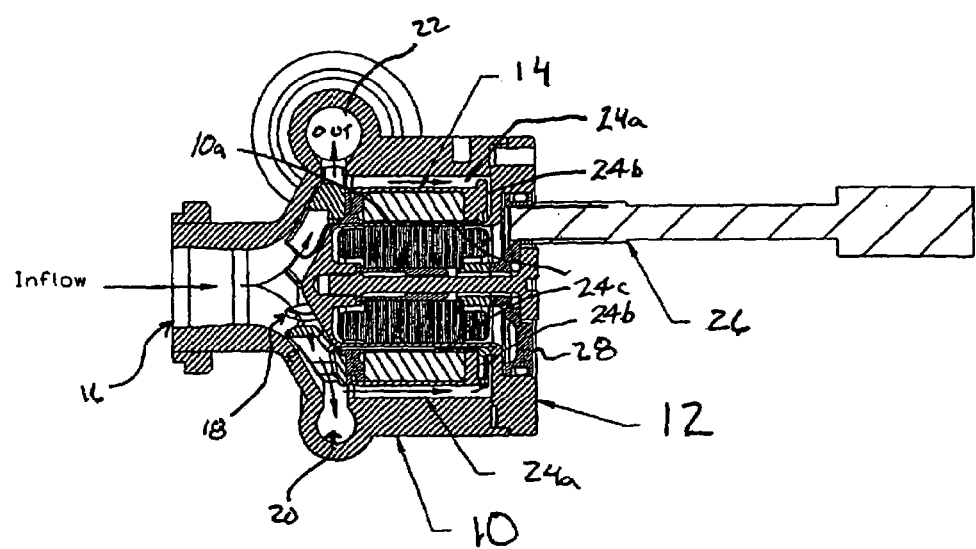
FIG. 1 is a cross-sectional view of a blood pump in accordance with the present invention.

With reference to FIG. 1, a centrifugal flow blood pump comprises three primary subassemblies, namely a volute housing assembly 10, a stator assembly 12, and a rotating assembly or rotor 14. Blood from a patient flows into an inlet port 16 of the blood pump. Arrows (unnumbered) indicate the direction of travel of the blood through the pump in the preferred embodiment. The blood specifically by primary impeller 18. The blood proceeds around the volute housing, first entering a volute channel 20 and a primary portion exiting the pump via a discharge port 22.

A small portion of the blood flows into a second channel or passage 24, specifically a first passage portion 24a that extends axially from a rear face of the primary impeller and is radially interposed between the rotor and a post formed by an axial extension 10a of the stator housing that protrudes into a pump chamber defined in the volute housing. As is well known, the chamber is in fluid communication with the inlet and outlet, and the primary impeller pumps the blood from the axial inlet to the tangential outlet. The secondary impeller (to be described in greater detail below) is provided at an opposite end of the rotor assembly remote from the primary impeller. A second passage portion 24b of the second channel defined at a second end of the rotor, i.e., remote from the primary impeller, continues from the first passage portion 24a and flows radially inward through the secondary impeller toward a rotational axis of the rotor. The small portion of blood flow then proceeds axially along a third passage portion 24c between the rotor 14 and the axial extension of the housing. The secondary channel thus forms a fluid or blood bearing that is continuously renewed during operation of the pump. Blood exits the bearing near the primary impeller 18 and is replenished by new blood flowing through the secondary channel 24.

As illustrated in FIG. 1, the cross-sectional dimension of the second channel varies from one portion to the next. Particularly, the channel has the largest dimension along the first portion 24a and the smallest dimension along the third portion 24c. The channel dimensions, in conjunction with the impeller geometry, speed, number of blades, clearance, pressure gradient, and flow recirculation, provide parameters for an effective fluid film bearing free of blood element deposition.

A jacketed cable 26 is received through a base portion 28 of the housing for connection with the stator assembly 12 contained in the axial extension. The cable carries power and control connections to and from the pump particularly to the stator assembly 12.

Figure 2A:
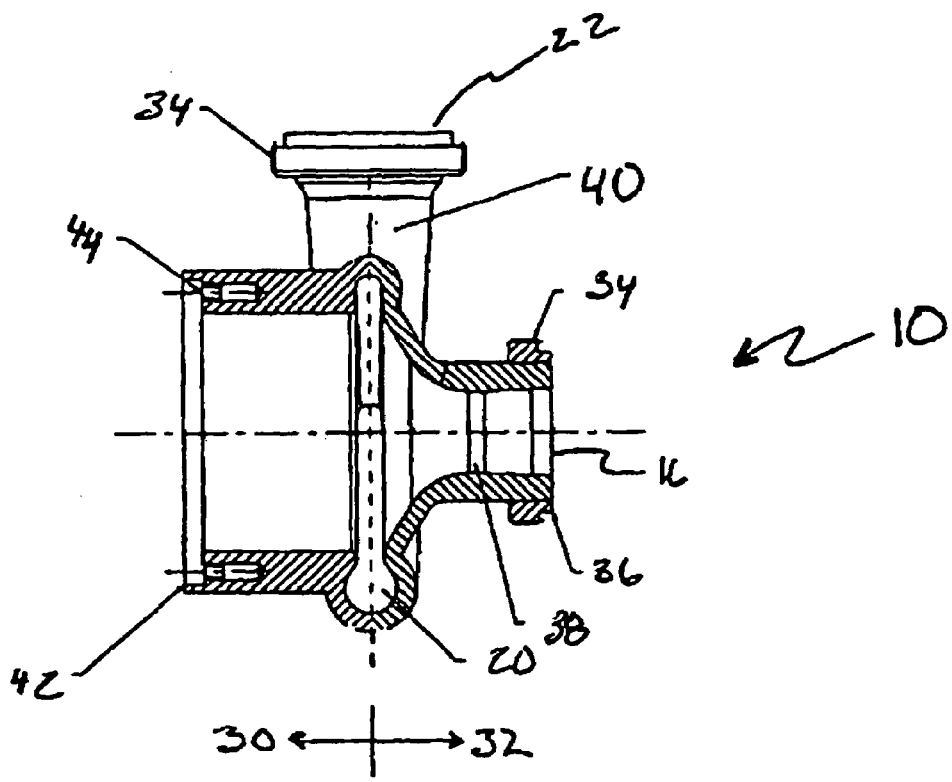
FIG. 2A is a cross-sectional view of a volute housing assembly in accordance with the present invention.
Figure 2B:
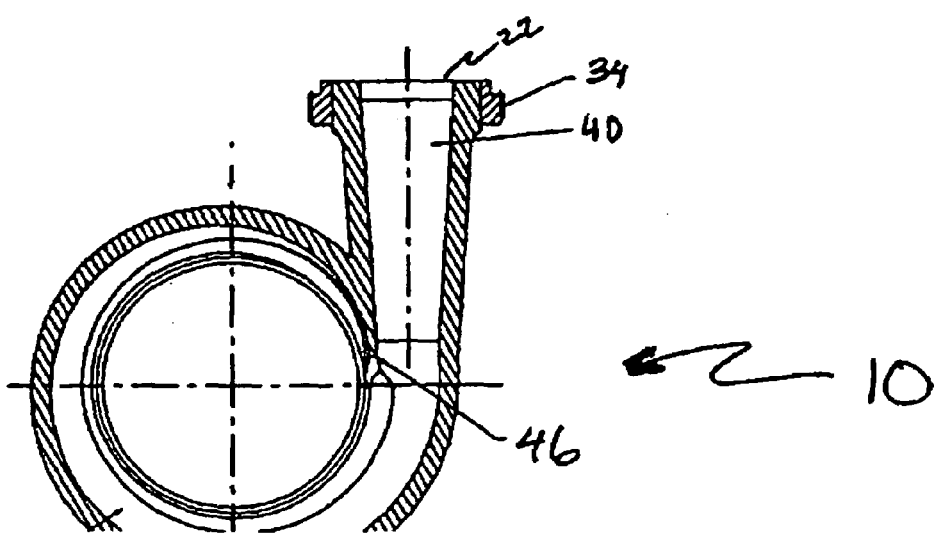
FIG. 2B is a cross-sectional view of the volute housing assembly taken generally along the lines 2B—2B of FIG. 2A.

With reference to FIGS. 2A and 2B, the volute housing assembly 10 in the preferred embodiment is formed by a single casting that is subsequently cut into two separate pieces before being joined again to form a one-piece housing. When separated, the individual pieces are machined and polished, removing any casting imperfections or anomalies within the volute section 20, prior to being welded together. Alternately, the volute housing assembly can be a single cast component, with no seams to weld. Preferably, the volute housing assembly 10 is made of titanium with walls approximately 2.5 mm thick. Both the inlet and discharge ports 16, 22 are configured for coupling 34 to adjacent fluid lines or passages. For example, the housing is externally threaded at each port for ease of connection with a corresponding female threaded coupling to provide a secure, sealed interconnection. The ports are preferably equipped with a guide surface or fitting pilot 36 for orienting connection to a fluid conduit (not shown).

The inlet port 16 communicates with an inlet throat 38 that has a slightly smaller diameter than the inlet port. In this manner, blood passes through the throat and is accelerated. This reduces pre-whirl of the blood entering the impeller 18. A conical diffuser 40 leading to the discharge port 22, and downstream of the primary channel, decreases the velocity of the pumped blood before it enters the aorta. In the preferred embodiment, the conical diffuser 40 widens to the discharge port 22 at an included angle of approximately 7°, although other diffuser angles and configurations can be used without departing from the scope and intent of the present invention.

A recess 42 is included in a base of the volute housing body 30. Inserts 44, are circumferentially spaced about the housing and adjusted to receive fasteners after the impeller assembly 14 and the stator assembly 12 have been inserted into the housing assembly. A volute tongue 46 extends inwardly from the housing along a tangent with the rotor to separate the diffuser from the pump chamber and direct the blood into the conical diffuser 40 at the end of the primary channel.

Figure 3:
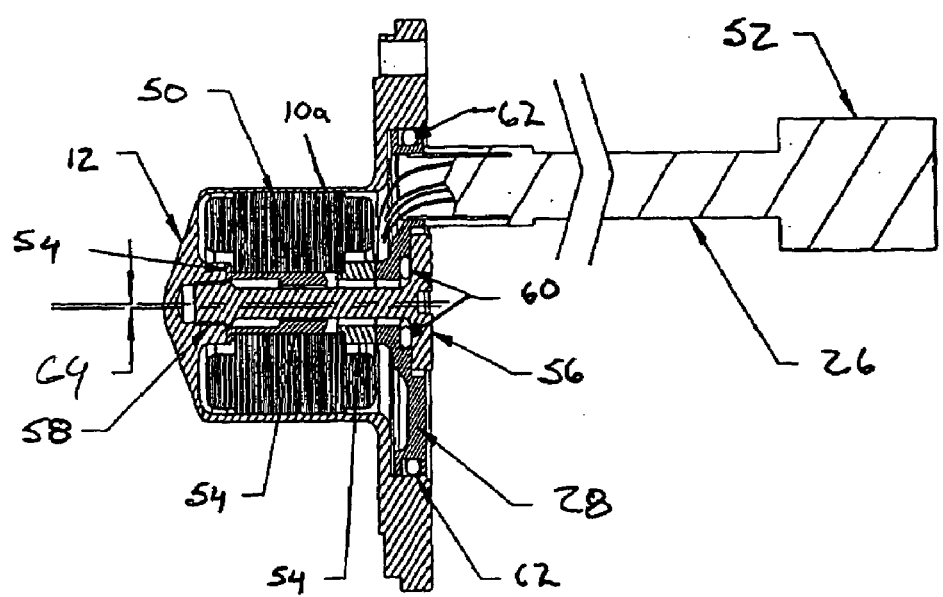
FIG. 3 is a cross-sectional view of a stator assembly in accordance with the present invention.

With reference to FIG. 3, stator windings 50 are located within the axial extension of the housing. An electrical connector 52 represented at a distal end of the jacketed cable 26 connects the pump to a power supply and control circuitry (not shown). In the preferred embodiment, the stator windings 50 are connected to the power supply which is located outside the body of the patient. The stator windings 50 and electrical connections are inserted into the stator housing axial extension and multiple inserts or shims 54 disposed about the stator windings 50, adjust position and ensure a tight and secure fit of the windings within the axial extension. The housing cover 28 is secured to the axial extension of the housing 10 with an attachment device 56, preferably a single fastener or screw that locks into a self-locking helical receptacle 58 at an opposite end of the axial extension. Seal members such as O-rings 60, 62 seal any possible apertures through which body fluids might enter the housing.

It will also be appreciated from a close examination of FIG. 3 that the stator assembly is offset within the axial extension. That is, the wall thickness of the axial extension differs over its circumferential extent. For example, the wall thickness along the top (as viewed in FIG. 3) is less than the wall thickness along the bottom. This provides a purposeful offset for controlling motion of the rotor and controlling the fluid film bearing formed between the rotor and housing. More particular details of this offset feature are shown and described in U.S. Pat. No. 5,324,177, which is hereby incorporated by reference.

FIGS. 4A and 4B illustrate three main features of the impeller assembly 14, namely the primary impeller 18, a secondary impeller 70, and an annular magnet 72. The primary impeller 18 includes multiple blades, e.g. seven blades, shaped such that together, the primary blades provide a mixed flow, i.e., combined axial and radial flow. The annular magnet 72 extends around a circumference of the impeller assembly 14 and mates with the post containing the stator windings 50 of the stator housing 12. The annular magnet 72 is preferably magnetized in a longitudinal, circumferentially spaced pattern, commonly known as a four pole pattern. Alternately, a plurality of individual magnets can be arranged in a similar pattern. The annular magnet 72 is inserted into the impeller assembly, sealing the magnet 72 within the rotor assembly envelope formed between the primary 18 and secondary 70 impellers. The assembly is welded or otherwise bonded shut.

Figures 5A, 5B:
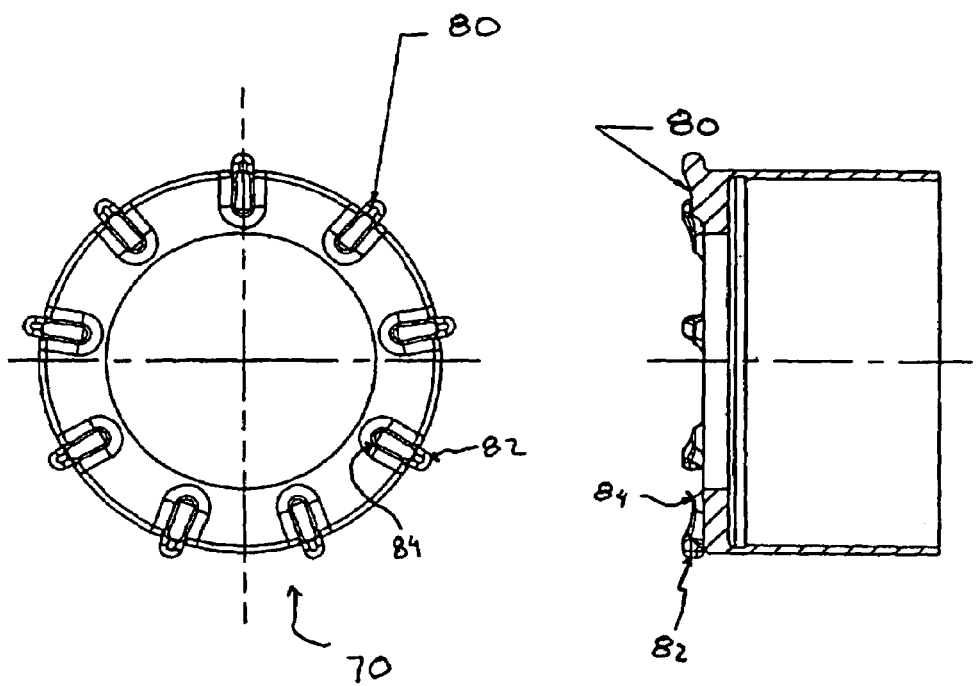
FIG. 5A is an elevational view of a secondary impeller in accordance with the present invention.
FIG. 5B is a cross-sectional view of the secondary impeller taken generally along the lines 5B—5B of FIG. 5A.

Details of the secondary impeller 70 disposed at one end or on a base of the impeller assembly 14, are more particularly illustrated in FIGS. 5A and 5B. The secondary impeller 70 comprises a plurality of straight, radial blades 80, nine blades in the preferred embodiment. Each blade 80 has a rounded outboard tip 82 that is approximately twice the height of a radial inner portion 84. The height difference is realized with a revolved scallop cut, shaping each of the blades 80 similarly. All transitions or edges of the blades are gradual, avoiding sharp corners or other crevices, wherein blood can become lodged. The preferred embodiment of the secondary impeller 70 as described establishes a rotorbalancing pressure distribution across the back of the rotating assembly while allowing a radial inflow of blood to continually wash through the secondary channel 24 between the impeller assembly 14 and the housing. The particular shape of the secondary impeller blades 80 keeps the blood moving to prevent stagnation/long residence times and the blades 80 free of thrombus formation.

In the preferred operation of the blood pump, the secondary impeller 70 establishes a radial pressure gradient across the base of the impeller assembly 14, such that control of rotating assembly hydraulic thrust and a differential pressure across the bearing is achieved. The pressure gradient and circulation of blood around the vanes help to avoid thrombus formation on the impeller and within the bearing.

The blood flow through the secondary channel 24 supplying the bearing is very low, relative to the flow through the primary channel 20. The design of the secondary impeller allows a balance between bearing flow, and creating too great an axial hydraulic loading. The thrust resulting from axial hydraulic loading is balanced by the axial magnetic stiffness of the motor components. The pressure at the outboard tips 82 of the blade is essentially equal to and fixed at the pressure at the primary impeller 18. A radial pressure gradient is created inboard of the secondary impeller tips. The higher the gradient, the lower the pressure at the secondary end of the bearing. If the pressure gradient is equal to the opposing primary impeller, then both the hydraulic thrust and the net bearing pressure and flow are zero. If the pressure gradient is too low, then both the bearing flow and hydraulic thrust on the impeller assembly 14 increases.

The invention has been described with reference to the preferred embodiment. Modifications and alterations will occur to others upon a reading and understanding of the preceding detailed description. It is intended that the invention be construed as including all such modifications and alterations insofar as they come within the scope of the appended claims or the equivalents thereof.

Having thus described the preferred embodiments, the invention is now claimed to be:

1. A cardiac assist device comprising:
a housing having an inlet and an outlet;
a rotor assembly adapted for rotation about a drive axis including a primary impeller for transporting blood from the inlet to the outlet, and a secondary impeller for cycling blood towards the inlet through a bearing interfaced between the rotor assembly and the housing, the secondary impeller having a series of spaced blades circumferentially spaced about the drive axis, the secondary impeller blades extending axially outwardly from the rotor assembly a greater dimension at a radial outer edge than a radial inner edge with a varying height over a radial dimension and having rounded edges.

2. The invention of claim 1 wherein the secondary impeller blades have a scalloped undercut whereby an outer radial portion of each blade extends outwardly a greater dimension than an inner radial portion of each blade.

3. The invention of claim 2 wherein the secondary impeller blades are disposed on a face of the rotor assembly and the scalloped undercut includes a concave surface extending inwardly in each blade from an outer radial edge to an inner radial edge.

4. The invention of claim 1 wherein each blade of the secondary impeller has a concave surface.

5. The invention of claim 1 further comprising an inverted motor and fluid film bearing including a stator received on a post formed by an axial extension of the housing and receiving an annular rotor having a drive magnet disposed therein that is radially supported and rotationally driven by the stator, a clearance defined between the annular rotor and housing extension defining a bearing that is supplied with a well-washed circulating flow of blood by the secondary impeller.

6. The invention of claim 5 wherein the rotor has an elongated axial dimension with the primary impeller located at a first end thereof and the secondary impeller located at a second end thereof.

7. The invention of claim 5 wherein the inlet extends axially and the outlet extends tangentially from the housing.

8. A blood pump having an improved bearing blood lubricated fluid film bearing, the blood pump comprising:
a housing having an inlet and outlet communicating with a pump chamber, and a portion extending into the chamber;
a rotor assembly received in the chamber for rotation about a drive axis and having a first impeller for pumping blood from the inlet to the outlet and a second impeller for maintaining blood flow through a fluid film bearing defined between an interface of the rotor assembly and housing, the second impeller including a set of blades extending radially outward from the drive axis and axially outward from the rotor assembly a greater dimension at a radial outer edge than a radial inner edge and each having rounded edges;
and stator winding and magnet ring components of a drive assembly for rotating the rotor assembly within the pump chamber.

9. The blood pump of claim 8 wherein the secondary impeller blades extend outwardly beyond the outer diameter of the rotor assembly.

10. The blood pump of claim 9 wherein the second impeller blades have a concave, rounded contour extending from the radial outer edge to the radial inner edge.

11. The blood pump of claim 8 wherein the drive assembly includes a stator winding disposed in the housing portion.

12. The blood pump of claim 11 wherein the drive assembly includes a magnet disposed in the rotor assembly.

13. The blood pump of claim 8 wherein the fluid film bearing includes a reduced dimensioned passageway interposed between the rotor assembly and the housing portion.

14. The blood pump of claim 13 wherein the housing portion is non-circular in cross-section.

15. The blood pump of claim 8 wherein radial inner portions of the second impeller blades are dimensioned to have a larger clearance with the housing than outer tips of the blades.

16. The blood pump of claim 15 wherein radial inner portions of the second impeller blades are approximately one-half the height of the outer tips of the blades.

* * * * *